US010604063B2

(12) United States Patent
Kita et al.

(10) Patent No.: US 10,604,063 B2
(45) Date of Patent: Mar. 31, 2020

(54) CONTROL DEVICE FOR VEHICLE HEADLIGHT

(71) Applicant: STANLEY ELECTRIC CO., LTD., Tokyo (JP)

(72) Inventors: Yasushi Kita, Tokyo (JP); Takako Kimura, Tokyo (JP); Mitsuhiro Uchida, Osaka (JP); Takeshi Waragaya, Tokyo (JP); Wataru Nakashima, Tokyo (JP)

(73) Assignee: STANLEY ELECTRIC CO., LTD., Tokyo (JP)

( * ) Notice: Subject to any disclaimer, the term of this patent is extended or adjusted under 35 U.S.C. 154(b) by 0 days.

(21) Appl. No.: 16/121,180

(22) Filed: Sep. 4, 2018

(65) Prior Publication Data

US 2019/0077305 A1 Mar. 14, 2019

(30) Foreign Application Priority Data

Sep. 8, 2017 (JP) ................... 2017-173141

(51) Int. Cl.
*B60Q 1/14* (2006.01)
*B60Q 1/24* (2006.01)
*G06K 9/00* (2006.01)
*A61B 5/00* (2006.01)
*B60Q 1/08* (2006.01)
*B60K 28/06* (2006.01)
(Continued)

(52) U.S. Cl.
CPC .............. *B60Q 1/1423* (2013.01); *A61B 5/18* (2013.01); *A61B 5/6893* (2013.01); *B60K 28/06* (2013.01); *B60Q 1/085* (2013.01); *B60Q 1/245* (2013.01); *B60W 40/08* (2013.01); *G06K 9/0061* (2013.01); *G06K 9/00288* (2013.01);
(Continued)

(58) Field of Classification Search
CPC ... B60Q 1/04; B60Q 1/26; B60Q 1/50; B60Q 1/1423; B60Q 1/143; B60Q 2300/054; B60Q 2300/41; B60Q 2300/43; G08G 1/16; G08G 1/166; G08G 1/0962; H05B 37/02; H05B 37/0218; H05B 37/0227;
(Continued)

(56) References Cited

U.S. PATENT DOCUMENTS 5,931,572 A 8/1999 Gotoh
7,616,104 B2 * 11/2009 Hara ...................... B60K 35/00
340/438

(Continued)

FOREIGN PATENT DOCUMENTS

DE 102005036002 A1 2/2007
DE 102013203925 A1 9/2014
(Continued)

OTHER PUBLICATIONS

Extended European Search Report for the related European Patent Application No. 18192594.2 dated Feb. 18, 2019.

*Primary Examiner* — Haissa Philogene
(74) *Attorney, Agent, or Firm* — Kenealy Vaidya LLP

(57) ABSTRACT

A control device for a vehicle headlight includes a motion information acquisition part that acquires information of a motion of at least a part of a driver in the vehicle, an attribute decision part that determines attribute of the driver based on the information acquired by the motion information acquisition part, and a light distribution controller that controls a light distribution of the vehicle headlight based on the attribute determined by the attribute decision part.

16 Claims, 5 Drawing Sheets

(51) Int. Cl.
*A61B 5/18* (2006.01)
*B60W 40/08* (2012.01)
*A61B 3/113* (2006.01)
*A61B 5/11* (2006.01)
*A61B 5/117* (2016.01)

(52) U.S. Cl.
CPC ..... *G06K 9/00375* (2013.01); *G06K 9/00604* (2013.01); *G06K 9/00845* (2013.01); *A61B 3/113* (2013.01); *A61B 5/0077* (2013.01); *A61B 5/117* (2013.01); *A61B 5/1114* (2013.01); *A61B 5/1128* (2013.01); *A61B 5/7475* (2013.01); *B60Q 2300/23* (2013.01); *B60W 2040/0809* (2013.01); *B60W 2040/0818* (2013.01); *B60W 2540/22* (2013.01); *B60W 2540/28* (2013.01); *G06K 9/00617* (2013.01)

(58) Field of Classification Search
CPC .. F21W 2102/00; A61B 5/0077; A61B 5/177; A61B 5/18; A61B 5/6893
See application file for complete search history.

(56) References Cited

U.S. PATENT DOCUMENTS

| | | | |
|---|---|---|---|
| 8,115,394 B2* | 2/2012 | Kobayashi | B60Q 1/085 315/158 |
| 8,606,459 B2* | 12/2013 | Sekiyama | B60R 16/0236 340/425.5 |
| 9,037,343 B2* | 5/2015 | Aimura | B60Q 1/085 340/435 |
| 9,469,240 B2* | 10/2016 | Uchida | B60Q 1/143 |
| 9,493,109 B2* | 11/2016 | Nordbruch | B60Q 1/085 |
| 9,682,703 B2* | 6/2017 | Okita | B60T 8/17558 |
| 10,134,283 B2* | 11/2018 | Masuda | B60Q 1/00 |
| 2005/0027419 A1* | 2/2005 | Horii | B60Q 1/12 701/49 |
| 2009/0016073 A1 | 1/2009 | Higgins-Luthman et al. | |
| 2013/0073114 A1 | 3/2013 | Nemat-Nasser et al. | |
| 2016/0090025 A1 | 3/2016 | Nagasawa | |
| 2016/0152173 A1 | 6/2016 | Mayer | |
| 2016/0176334 A1 | 6/2016 | Roeckl et al. | |
| 2016/0207443 A1* | 7/2016 | Widdowson | B60Q 1/0011 |
| 2017/0267238 A1* | 9/2017 | Mimura | B60W 50/14 |

FOREIGN PATENT DOCUMENTS

| | | |
|---|---|---|
| DE | 102014005028 A1 | 9/2014 |
| DE | 102014205864 A1 | 10/2015 |
| DE | 102016001692 A1 | 8/2017 |
| EP | 2384930 A1 | 11/2011 |
| JP | 2009-120149 A | 6/2009 |
| JP | 2010-036779 A | 2/2010 |
| WO | 2008056679 A1 | 5/2008 |
| WO | 2013114828 A1 | 8/2013 |
| WO | 2016082104 A1 | 6/2016 |

\* cited by examiner

CONTROL DEVICE FOR VEHICLE HEADLIGHT

CROSS-REFERENCE TO RELATED APPLICATION

Priority is claimed on Japanese Patent Application No. 2017-173141, filed Sep. 8, 2017, the content of which is incorporated herein by reference.

BACKGROUND

Field of the Invention

The present invention relates to a control device for a vehicle headlight.

Description of Related Art

Headlights for an automobile have, for example, two functions of a traveling beam (a so-called high beam) and a passing beam (a so-called low beam).

In recent years, an adaptive driving beam (ADB) has been developed, and a light having a function of blocking some of light to a preceding vehicle or an oncoming vehicle present in front of a vehicle and having a function of holding a region of a traveling beam has been registered.

In the ADB, when a side in front of a vehicle is photographed by a camera and an object of which light should be blocked is detected, a signal is sent to a light control module (LCM) and light is blocked such that the light does not reach the object.

In addition, an apparatus for varying a light distribution according to attributes of a driver in a vehicle has been developed (for example, see Japanese Unexamined Patent Application, First Publication No. 2010-36779). In the technology disclosed in Japanese Unexamined Patent Application, First Publication No. 2010-36779, attributes of a driver are determined on the basis of driving operation information (an accelerator operation amount, a brake operation amount, a steering operation amount, a vehicle speed, an acceleration and a steering torque) and a captured image of the driver, and control of radiation of light according to the attributes of the driver is performed. In the technology disclosed in Japanese Unexamined Patent Application, First Publication No. 2010-36779, for example, a light quantity, a radiation range (including an angle of aim) and a swivel speed of the light distribution are varied.

However, in the related art, it may be difficult to accurately determine attributes of a driver.

For example, in the related art, when the attribute of the driver is determine, the motion of the driver may not be sufficiently taken into account.

SUMMARY OF THE INVENTION

As described above, in the related art, it may be difficult to accurately determine attributes of a driver.

An aspect of the present invention is directed to providing a control device for a vehicle headlight capable of accurately deciding attributes of a driver.

A control device for a vehicle headlight according to an aspect of the present invention includes a motion information acquisition part that acquires information of a motion of at least a part of a driver in the vehicle; an attribute decision part that determines attribute of the driver based on the information acquired by the motion information acquisition part; and a light distribution controller that controls a light distribution of the vehicle headlight based on the attribute determined by the attribute decision part.

According to the above mentioned aspect of the present invention, the control device for a vehicle headlight may include a vehicle outside information acquisition part that acquires information regarding outside of the vehicle, wherein, when determining the attribute, the attribute decision part may determine the attribute of the driver based on at least one of the information acquired by the motion information acquisition part and the information acquired by the vehicle outside information acquisition part.

According to the above mentioned aspect of the present invention, the control device for a vehicle headlight may include a driver identification part that identifies the driver, wherein, when determining the attribute, the attribute decision part may determine the attribute of the driver based on at least one of the information acquired by the motion information acquisition part and past information regarding the driver identified by the driver identification part.

According to the above mentioned aspect of the present invention, the control device for a vehicle headlight may include a driver identification part that identifies the driver, wherein, when determining the attribute, the attribute decision part may determine the attribute of the driver based on at least one of the information acquired by the motion information acquisition part, the information acquired by the vehicle outside information acquisition part and past information regarding the driver identified by the driver identification part.

According to the above mentioned aspect of the present invention, the motion information acquisition part may include at least one of a sight line information acquisition part that acquires information related to a sight line of the driver, a driver action information acquisition part that acquires information related to an action of the driver, a face direction angular speed information acquisition part that acquires information related to a direction of the driver's face.

According to the above mentioned aspect of the present invention, the vehicle outside information acquisition part may include at least one of a photographing information acquisition part that acquires information of a captured image and an object information acquisition part that acquires information related to an object present outside of the vehicle.

A vehicle headlight according to another aspect of the present invention includes a headlight that is capable of variably changing a light distribution, and the control device for a vehicle headlight according to the above mentioned aspect of the present application that controls the headlight.

According to the aspect of the present invention, attributes of a driver can be accurately determine.

DETAILED DESCRIPTION OF THE INVENTION

Hereinafter, an embodiment of the present invention will be described with reference to the accompanying drawings.

In the embodiment, while an automobile is exemplified as an example of a vehicle, a motorcycle or the like may be provided as the vehicle.

Schematic Configuration of Automobile

Figure 1:
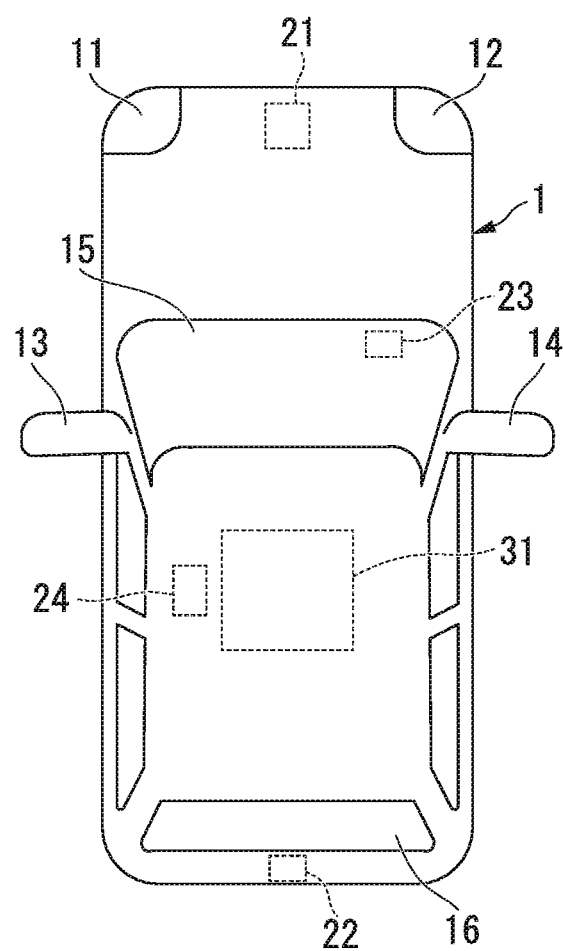
FIG. 1 is a view showing a schematic configuration of an automobile according to an embodiment of the present invention.

FIG. 1 is a view showing a schematic configuration of an automobile 1 according to an embodiment of the present invention.

The automobile 1 includes a headlight on the left side (in the embodiment, referred to as a left headlight 11), a headlight on the right side (in the embodiment, referred to as a right headlight 12), a side mirror on the left side (in the embodiment, referred to as a left side mirror 13), a side mirror on the right side (in the embodiment, referred to as a right side mirror 14), a front window 15, and a rear window 16.

The left headlight 11 is disposed on the left side on the front of the automobile 1, and the right headlight 12 is disposed on the right side on the front of the automobile 1.

In addition, the automobile 1 includes a vehicle outside detector (in the embodiment, referred to as a vehicle front outside detector 21) on the front side, a vehicle outside detector (in the embodiment, referred to as a vehicle rear outside detector 22) on the rear side, a vehicle inside detector 23, a vehicle information detector 24, and a controller 31.

Here, while some of constituent components of the automobile 1 are shown in the embodiment, for example, in addition thereto, arbitrary constituent components such as another constituent component or the like normally included in a general automobile may be provided.

In addition, some or all of the vehicle front outside detector 21, the vehicle rear outside detector 22, the vehicle inside detector 23, the vehicle information detector 24 and the controller 31 may be provided in the automobile 1 without being able to be seen from the appearance of the automobile 1.

Schematic Functional Configuration of Control System of Automobile

Figure 2:
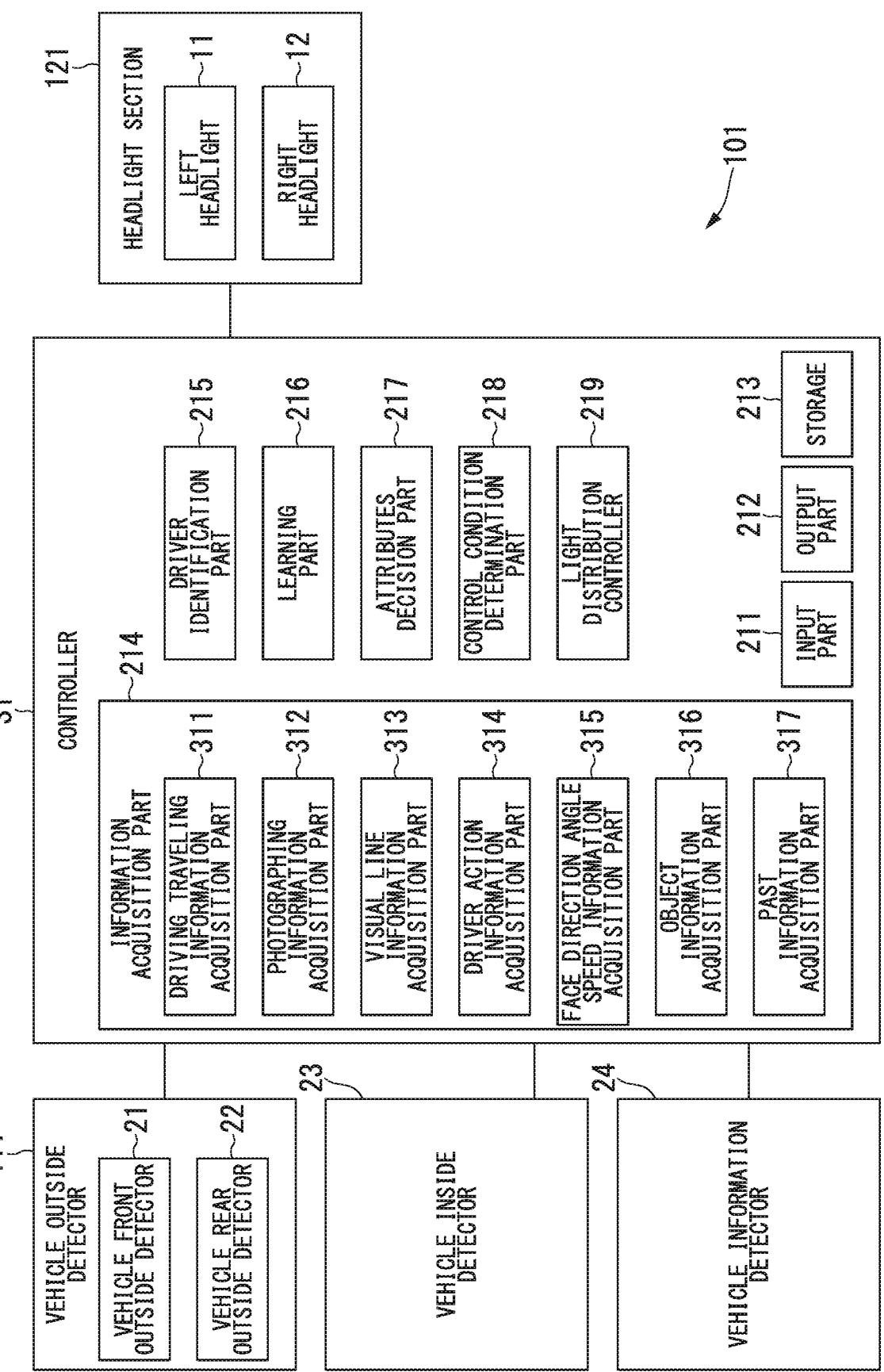
FIG. 2 is a functional block diagram showing a schematic functional configuration of a headlight control system provided in an automobile according to the embodiment of the present invention.

FIG. 2 is a functional block diagram showing a schematic functional configuration of a headlight control system 101 included in the automobile 1 according to an embodiment of the present invention.

The headlight control system 101 includes a vehicle outside detector 111, the vehicle inside detector 23, the vehicle information detector 24, a headlight section 121 (headlight unit) and the controller 31.

The vehicle outside detector 111 includes the vehicle front outside detector 21 and the vehicle rear outside detector 22.

Here, the vehicle front outside detector 21, the vehicle rear outside detector 22, the vehicle inside detector 23, the vehicle information detector 24 and the controller 31, which are shown in FIG. 2, are the same as those shown in FIG. 1.

The vehicle outside detector 111 detects information related to an outside of the automobile 1 (in the embodiment, referred to as "a vehicle outside").

The vehicle front outside detector 21 detects information related to an outside in front of the automobile 1.

The vehicle rear outside detector 22 detects information related to an outside in rear of the automobile 1.

Here, in the embodiment, like in the general concept of "front and rear," a direction in which the automobile 1 generally advances, which is a direction in which a driver in the automobile 1 generally faces, is referred to as "in front (forward)" and a direction opposite thereto is referred to as "in rear (rearward)."

In addition, while the automobile 1 includes the vehicle front outside detector 21 and the vehicle rear outside detector 22 in the embodiment, one or both of them may not be provided in another configuration example.

In addition, as another configuration example, the automobile 1 may include a vehicle outside detector configured to detect information related to outside to a side of the automobile 1 (in the embodiment, referred to as "a vehicle side outside detector). As the vehicle side outside detector, for example, a vehicle side outside detector on the right side with respect to a direction of advance of the automobile 1 and a vehicle side outside detector on the left side with respect to the advance direction of the automobile 1 may be used.

The vehicle front outside detector 21 may include a detector configured to detect arbitrary information related outside in front of the vehicle. The vehicle front outside detector 21 may include one or more of, for example, light detection and ranging (LiDAR), radar, and sonar devices, and a camera (an imaging device), and so on. The camera or the like may have, for example, a function of detecting visible light, may include a function of detecting infrared light, or may include both of these.

Similarly, the vehicle rear outside detector 22 may include a detector configured to detect arbitrary information related to outside in rear of the vehicle.

Further, when the vehicle side outside detector is provided, similarly, the vehicle side outside detector may include a detector configured to detect arbitrary information related to an outside of a side of the vehicle.

Here, with respect to a predetermined object, the detector having a LiDAR function can detect, for example, information related to a distance between the detector and the object or information related to properties of the object by using electromagnetic waves having a short wavelength.

With respect to a predetermined object, the detector having a radar function can detect, for example, information related to a distance between the detector and the object or information related to a direction of the object when seen from the detector by using radio waves.

The detector having a sonar function can detect, for example, information related to a predetermined object by using sonic waves.

The camera can detect, for example, information of an image obtained by photographing a predetermined object.

The vehicle inside detector 23 detects information related to an inside (in a passenger compartment) of the automobile 1. In the embodiment, the vehicle inside detector 23 detects information related to a portion having a driver's seat (a cockpit) on which a driver sits.

The vehicle inside detector 23 may include a detector configured to detect arbitrary information related to the inside of the vehicle. The vehicle inside detector 23 may include, for example, one or more of LiDAR, radar, sonar, a sight line sensor, a camera (an imaging device), and so on. For example, the camera or the like may include a function of detecting visible light, may include a function of detecting infrared light, or may include both of them.

Here, for example, with respect to a predetermined object (in the embodiment, a driver), the detector having a function of LiDAR can detect information related to a distance between the detector and the object or information related to a character of the object by using electromagnetic waves having a short wavelength.

For example, with respect to a predetermined object (in the embodiment, a driver), the detector having a function of radar can detect information related to a distance between the detector and the object or information related to a direction of the object when seen from the detector by using radio waves.

For example, the detector having a function of sonar can detect information related to a predetermined object by using sonic waves.

The detector having a function of a sight line sensor can detect information related to a sight line of a person (in the embodiment, a sight line of a driver who is sitting on a driver's seat). The information related to a sight line of a person may be so-called eye-tracking information.

For example, the camera can detect information of an image obtained by photographing a predetermined object (in the embodiment, a driver).

The vehicle information detector 24 detects information related to the automobile 1 (a vehicle).

The vehicle information detector 24 may detect arbitrary information related to the automobile 1 (the vehicle). The vehicle information detector 24 may include one or more of, for example, a sensor configured to detect information related to an operation amount of an accelerator, a sensor configured to detect information related to an operation amount of a brake, a sensor configured to detect information related to an operation amount of a steering wheel (for example, a so-called handle), a sensor configured to detect information related to a speed (a vehicle speed) of the automobile 1, a sensor configured to detect information related to an acceleration of the automobile 1, and a sensor configured to detect information related to a steering torque of the automobile 1.

Further, the sensor configured to detect information related to a speed or an acceleration of the automobile 1 may have, for example, a function of detecting information related to a rotational speed of wheels (tires) of the automobile 1. In addition, the sensor configured to detect information related to a steering torque of the automobile 1 may have, for example, a function of detecting information related to a torque generated between the wheels of the automobile 1 and a road surface.

The headlight section 121 is a so-called headlamp, which radiates light to a side in front of the automobile 1.

The left headlight 11 radiates light to a left side in front of the automobile 1.

The right headlight 12 radiates light to a right side in front of the automobile 1.

Here, in the embodiment, the left headlight 11 and the right headlight 12 have a function of radiating light of a traveling beam (a so-called high beam) and a function of radiating light of a passing beam (a so-called low beam), and the two functions may be switched between.

Further, arbitrary lamps may be used as the left headlight 11 and the right headlight 12.

As a specific example, for example, one or more of a traveling beam lamp, a passing beam lamp, a micro electro mechanical system (MEMS) laser scanning headlamp, a digital mirror device (DMD) headlamp, a matrix ADB headlamp that can control rows and columns, an ADB headlamp that can control only columns, and so on, may be used as the lamps.

Here, for example, the MEMS laser scanning headlamp is an example of a headlamp for a vehicle that can variably change a light distribution, and an example of a seamless ADB lamp.

The controller 31 includes an input part 211, an output part 212, a storage 213, an information acquisition part 214, a driver identification part 215, a learning part 216, an attribute decision part 217, a control condition determination part 218 and a light distribution controller 219.

The information acquisition part 214 includes a driving traveling information acquisition part 311, a photographing information acquisition part 312, a sight line information acquisition part 313, a driver action information acquisition part 314, a face direction angular speed information acquisition part 315, an object information acquisition part 316 and a past information acquisition part 317.

The input part 211 inputs information from the outside of the automobile 1. As an example, the input part 211 has an operation section that can be operated by a user (a person), and inputs information according to an operation performed with respect to the operation section. As another example, the input part 211 may input information output from an external apparatus. The user may be, for example, a driver or an occupant in the automobile 1.

The output part 212 outputs information to the outside of the automobile 1. As an example, the output part 212 may output display information to a screen (display output). As another example, the output part 212 may output sound information from a speaker (sound output). As another example, the output part 212 may output information to an external apparatus.

The storage 213 stores information.

Here, the storage 213 may store arbitrary information.

As an example, the storage 213 may store information such as a control program, control parameters, or the like, which is executed by the controller 31. In this case, the controller 31 includes a processor such as a central processing unit (CPU) or the like, and the processor executes various kinds of processing by executing the control program stored in the storage 213 using the control parameters stored in the storage 213.

As another example, the storage 213 may store past information or may store, for example, information obtained by the information acquisition part 214 in the past, information obtained from processing in the controller 31 in the past, or the like.

The information acquisition part 214 acquires various kinds of information. In the embodiment, the information acquisition part 214 acquires information detected by the vehicle outside detector 111 (the vehicle front outside detector 21 or the vehicle rear outside detector 22), information detected by the vehicle inside detector 23, or information detected by the vehicle information detector 24.

The driving traveling information acquisition part 311 acquires information related to driving of the automobile 1 or traveling of the automobile 1. In the embodiment, the driving traveling information acquisition part 311 acquires information detected by the vehicle information detector 24, and acquires one or more of, for example, information related to an operation amount of an accelerator, information related to an operation amount of a brake, information related to an operation amount of a steering wheel, information related to a vehicle speed of the automobile 1, information related to an acceleration of the automobile 1, information, related to a steering torque of the automobile 1, and so on.

Here, the information related to an operation amount of a brake may include, for example, information related to an operation (a sudden braking operation) in which a variation of an operation amount of a brake within a predetermined time is a predetermined threshold value or more.

In addition, the information related to an operation amount of a steering wheel may include, for example, information of a frequency of an operation amount of a steering wheel.

In addition, the information related to an operation amount of a steering wheel may include, for example, information of an angular speed when an operation amount of a steering wheel corresponds to an angle.

The photographing information acquisition part 312 acquires information of a captured image. In the embodiment, the photographing information acquisition part 312 acquires one or more of photographing information detected by the camera of the vehicle front outside detector 21 (information of an image obtained by photographing a side in front of the automobile 1), photographing information detected by the camera of the vehicle rear outside detector 22 (information of an image obtained by photographing a side in rear of the automobile 1), and photographing information detected by the camera of the vehicle inside detector 23 (information of an image obtained by photographing an inside of the automobile 1).

The sight line information acquisition part 313 acquires information related to a sight line of a driver (in the embodiment, referred to as "sight line information"). In the embodiment, the sight line information acquisition part 313 acquires information detected by the sight line sensor of the vehicle information detector 24.

Here, the sight line information is information based on a motion of a driver's eyes (for example, eyeballs), and information related to a motion of at least a part of a driver (a part of the body).

The driver action information acquisition part 314 acquires information related to an action of a driver. In the embodiment, the driver action information acquisition part 314 acquires, for example, information related to an action of a driver, which is information detected by one or more of the LiDAR, the radar, the sonar and the camera of the vehicle information detector 24.

Here, the information related to an action of a driver is information based on a motion of a part (a part of the body) or all (all of the body) of the driver, and information related to a motion of at least a part of the driver. For example, the head, the neck, the shoulders, the trunk, the arms, the hands, the fingers, the legs, the feet, or the like, may be at least a part of the driver.

The face direction angular speed information acquisition part 315 acquires information related to an angular speed of an angle corresponding to a direction of a driver's face (in the embodiment, referred to as "a face direction angular speed"). In the embodiment, the face direction angular speed information acquisition part 315 acquires, for example, information related to the face direction angular speed, which is information detected by one or more of the LiDAR, the radar, the sonar and the camera of the vehicle information detector 24. A direction of a driver's face varies, for example, according to a motion of the driver's face.

Here, the information related to a face direction angular speed is information based on a motion of a driver's face, and information related to a motion of at least a part of a driver (a part of the body).

Further, a function of the sight line information acquisition part 313 may be included in, for example, a function of the driver action information acquisition part 314 as a function provided in the driver action information acquisition part 314.

In addition, a function of the face direction angular speed information acquisition part 315 may be included in, for example, a function of the driver action information acquisition part 314 as a function provided in the driver action information acquisition part 314.

That is, the driver action information acquisition part 314 may acquire information related to a sight line of a driver, or information related to a direction of a driver's face.

The object information acquisition part 316 acquires information related to an object present outside of the automobile 1. In the embodiment, the object information acquisition part 316 acquires, for example, information related to a substance present in the outside of the automobile 1, which is information detected by one or more of the LiDAR, the radar and the sonar of the vehicle outside detector 111 (the vehicle front outside detector 21 and the vehicle rear outside detector 22).

The past information acquisition part 317 acquires past information. In the embodiment, the past information acquisition part 317 acquires the past information stored in the storage 213.

Here, information obtained by combining two or more acquired pieces of information may be acquired by the information acquisition part 214.

For example, based on the information acquired by the sight line information acquisition part 313 and the information acquired by the photographing information acquisition part 312, information on an object present in the direction in which the sight line of the driver is facing (an object seen by the driver) may also be acquired. As a specific example thereof, by superimposing the direction of the sight line on the captured image, an object present in the direction of the sight line can be recognized.

For example, information related to a substance present in a direction to which a sight line of a driver is directed (a substance seen by a driver) may be acquired on the basis of the information acquired by the sight line information acquisition part 313 and the information acquired by the object information acquisition part 316. As a specific example, it is possible to recognize a substance present in a direction of a sight line by overlapping the direction of the sight line and disposition of the substance (an object).

For example, information related to a substance present in a direction to which a driver's face is directed (a substance considered to be seen by a driver) may be acquired on the basis of the information acquired by the face direction angular speed information acquisition part 315 and the information acquired by the photographing information acquisition part 312. As a specific example, it is possible to recognize a substance present in a direction of a face by overlapping the direction of the face and the captured image.

For example, information related to a substance present in a direction to which a driver's face is directed (a substance considered to be seen by a driver) may be acquired on the basis of the information acquired by the face direction angular speed information acquisition part 315 and the information acquired by the object information acquisition part 316. As a specific example, it is possible to recognize a substance present in a direction of a face by overlapping the direction of the face and disposition of the substance (a substance).

The driver identification part 215 identifies a driver in the automobile 1. For example, the driver identification part 215 may identify a new driver, or may identify a driver having a past usage record (usage history, or the like) in the past.

As an example, the driver identification part 215 may identify a driver on the basis of the information input by the input part 211. For example, information for identifying each driver (also referred to as a "driver ID" in the present embodiment) may be input by each driver (or another person) operating an operation unit (for example, the operation unit of the input part 211).

In addition, the driver identification part 215 may store the driver ID and information on the driver corresponding to the driver ID in the storage 213 in association with each other. Regarding the information on the driver, arbitrary information may be used, and for example, one or more of pieces of information on a name, sex, age, driving experience, other attributes, and the like, may be used.

As another example, the driver identification part 215 may identify a driver on the basis of the information acquired by the information acquisition part 214. For example, the driver identification part 215 may identify a driver using a technology of biometric authentication. Specifically, the driver identification part 215 may identify a driver on the basis of feature information such as a driver's face or pupils.

In addition, the driver identification part 215 may store the feature information of the driver and the driver-related information in association with each other in the storage 213.

Here, when the feature information of the driver and driver ID are associated with each other, the driver identification part 215 may associate the driver ID, the feature information of the driver, and the driver-related information with each other and store the association in the storage 213. In this case, for example, the driver identification part 215 can identify both of a driver on the basis of the driver IDs and a driver on the basis of the information acquired by the information acquisition part 214 (the feature information of the driver).

As an example, the driver identification part 215 may identify a driver when information related to the driver is input by the driver or the like. As another example, the driver identification part 215 may automatically identify a driver when it is automatically detected that the driver has sat on a driver's seat.

In addition, as an example, the driver identification part 215 may release a state in which a driver is being identified when information showing termination of driving is input by the driver or the like. As another example, the driver identification part 215 may automatically release a state in which a driver is being identified when it is automatically detected that the driver got off the driver's seat.

The learning part 216 performs mechanical learning on predetermined information for each driver. For example, information related to an operation of the automobile 1 performed by a driver is used as the predetermined information. The learning part 216 may perform learning on the basis of, for example, with respect to a driver as a target, past information related to the driver acquired by the past information acquisition part 317 and current information related to the driver acquired by the driving traveling information acquisition part 311.

Here, the learning part 216 may perform learning at each driver recognized by the driver identification part 215.

In addition, for example, the learning part 216 may include a function of artificial intelligence (AI).

The attribute decision part 217 determines attributes (may be referred to as "personality") of a driver in the automobile 1.

Here, the attribute decision part 217 may determine attributes of a driver on the basis of the arbitrary information acquired by the information acquisition part 214.

In addition, the attribute decision part 217 may determine attributes of a driver on the basis of one piece of information acquired by the information acquisition part 214, or determine attributes of a driver on the basis of two or more pieces of information acquired by the information acquisition part 214 (for example, a combination of two or more pieces of information).

For example, the attribute decision part 217 may determine attributes of a driver on the basis of information of a motion of a part or all of the driver's body.

Here, the information of a motion of a part or all of the driver's body may be obtained on the basis of information acquired by an arbitrary one or more of, for example, the photographing information acquisition part 312, the sight line information acquisition part 313, the driver action information acquisition part 314 and the face direction angular speed information acquisition part 315.

As an example, the attribute decision part 217 may determine attributes of a driver on the basis of sight line information of the driver. The sight line information of the driver is, for example, information based on movement of the driver's eyeballs.

For example, based on the information on the sight line of the driver when the driver is driving the automobile 1, the attribute decision part 217 may calculate the count number or time of looking to the side in front of the automobile 1 (the direction of the sight line is facing forward) during elapse of a predetermined time and the attributes of the driver may be determine according to the calculation results (count number or time).

Regarding the side in front of the automobile 1, for example, information identifying a corresponding area (the area in front of the automobile 1) is stored in the storage 213 and used by the attribute decision part 217.

In addition, the fact that the driver sees a side in front of the automobile 1 may be determine by, for example, sight line information of the driver, or may be specified by the sight line information of the driver and other information. For example, one or more of image information from in front of the automobile 1, image information of a driver, and information related to an action of a driver may be used as the other information.

In addition, the count in the predetermined time may be regarded as, for example, a frequency.

For example, the attribute decision part 217 may calculate a count number or a time when a driver sees a predetermined mirror (when a sight line is directed) while a predetermined time elapses (for example, a certain time) on the basis of the information of the sight line of the driver when the driver drives the automobile 1.

The attributes of the driver may be determine according to the calculated result (the count number or the time). For example, a windshield rearview mirror, a rearview mirror, or a side mirror (the left side mirror 13 or the right side mirror 14) may be used as the predetermined mirror.

For example, the attribute decision part 217 may calculate a count number or a time when a driver sees a speed indicator (when a sight line is directed) while a predetermined time (for example, a certain time) elapses on the basis of the information of the sight line of the driver when the driver drives the automobile 1, and may determine the attributes of the driver according to the calculated result (the count number or the time).

For example, the attribute decision part 217 may determine attributes of a driver according to an amount of time when the sight line of the driver is continuously present within a predetermined range (a time for which a sight line is maintained) on the basis of the information of the sight line of the driver when the driver drives the automobile 1. Here, for example, the predetermined range may be a range that was previously determined, or may be a range set on the basis of the information of the sight line of the driver. The range set on the basis of the information of the sight line of the driver may be, for example, a range set with reference to a position of the sight line of the driver when measuring of the staring time of the sight line is started.

The attribute decision part 217 may determine, for example, attributes of a driver according to a position when a sight line of the driver is continuously present at the same position for a predetermined time or more (the retention position of the sight line) on the basis of the information of the sight line of the driver when the driver drives the automobile 1. Here, in a method of deciding whether or not the position of the sight line is the same position, for example, even if the position of the sight line is not completely the same position, if a change (deviation) in the position of the sight line falls within a predetermined range, this may be considered to be the same position.

For example, the attribute decision part 217 calculates a count number or a time when a driver sees a predetermined substance outside the vehicle (when a sight line is directed) while a predetermined time (a certain time) elapses on the basis of the information of the sight line of the driver when the driver drives the automobile 1, and may determine attributes of the driver according to the calculated result (the count number or the time). For example, a traffic signal or a marking such as a white line or the like may be used as the predetermined substance.

Here, for example, the attribute decision part 217 may specify the predetermined substance as a traffic signal, a white line, or the like, on the basis of one or both of the information acquired by the photographing information acquisition part 312 and the information acquired by the object information acquisition part 316.

As an example, the attribute decision part 217 may determine attributes of a driver on the basis of information of a distance (an inter-vehicle distance) between the host vehicle (the automobile 1) operated by the driver and another automobile.

Here, for example, the attribute decision part 217 may specify presence of another automobile and a distance (an inter-vehicle distance) between the host vehicle (the automobile 1) and the other automobile on the basis of one or both of the information acquired by the photographing information acquisition part 312 and the information acquired by the object information acquisition part 316.

As an example, the attribute decision part 217 may determine the attributes of the driver based on the information of a differential value (angular velocity) with respect to the steering angle of the steering wheel. Here, the differential value (angular velocity) with respect to the steering angle of the steering wheel can be regarded as, for example, blurring of the steering wheel (so-called steering wheel shake).

Here, for example, the information of the differential value (the angular speed) of the steering angle of the steering wheel is obtained on the basis of the information acquired by the driving traveling information acquisition part 311.

As an example, the attribute decision part 217 may determine attributes of a driver on the basis of the information of the timing when the automobile 1 starts upon turning right.

Here, for example, the information of the timing when the automobile 1 starts upon turning right is obtained on the basis of the information acquired by the driving traveling information acquisition part 311.

As an example, the attribute decision part 217 may determine attributes of a driver on the basis of information of a degree of the deceleration of the automobile 1.

Here, for example, the information of the degree of the deceleration of the automobile 1 is obtained on the basis of the information acquired by the driving traveling information acquisition part 311.

As an example, the attribute decision part 217 may determine attributes of a driver on the basis of information of a place at which the automobile 1 is traveling. For example, as the information of the place at which the automobile 1 is traveling, information of the place at which the automobile 1 is traveling on a surface of a road may be used, or as a specific example, information that shows a left side, a center, a right side, or the like, in a lane width may be used.

Here, the information of the place at which the automobile 1 is traveling is obtained on the basis of one or both of, for example, the information acquired by the photographing information acquisition part 312 and the information acquired by the object information acquisition part 316. As a specific example, a white line (a position or the like of the white line) in the road can be specified on the basis of the information acquired by the photographing information acquisition part 312.

As an example, the attribute decision part 217 may determine attributes of a driver on the basis of past information. For example, information acquired by the past information acquisition part 317 may be used as the past information.

As an example, the attribute decision part 217 may determine the attributes of the driver based on past information and current information. In this case, for example, for the same driver, information acquired when the driver operated the automobile 1 before the previous time may be used as past information, and for the current information, information acquired when the driver is currently operating the automobile 1 may be used.

Here, for example, an operation from the driver boarding and starting driving of the automobile 1 to the end of driving and disembarking from the vehicle 1 may be a single operation (one instance of driving) of the automobile 1, or alternatively, from the time the engine of the vehicle 1 is turned on until it is turned off may be a single operation (one instance of driving) of the automobile 1, or another manner may be used.

A specific example of attributes and decision will be described.

Here, first attribute, second attribute and third attribute are considered. The first attribute is attribute referred to as "a beginner." The second attribute is attribute referred to as "an elderly people." The third attribute is attribute referred to as "a general driver."

For example, the attribute decision part 217 may determine that the attribute of the driver is the first attribute, in a case a count number or an amount of time (may be a count number or an amount of time within a predetermined time) in which a position (a gazing position) of a sight line of the driver is directed in front of the automobile 1 or at a road shoulder (or at the vicinity of the road shoulder) exceeds a predetermined threshold value or a count number or an amount of time (may be a count number or an amount of time within a predetermined time) in which a range (a gazing range) including the position to which a sight line of the driver is directed is present in front of the automobile 1 or at a road shoulder (or at the vicinity of the road shoulder) exceeds a predetermined threshold value.

In general, when the driver is a beginner, it is likely to have a narrow field of vision range (a range before the sight line) in a front side seen by the driver.

For example, the attribute decision part 217 may determine that the attribute of the driver is the first attribute when a count number or an amount of time (may be a count number or an amount of time for a predetermined time) in which the driver sees a predetermined mirror is less than a predetermined threshold value. In general, when the driver is a beginner, a frequency that the driver sees a windshield rearview mirror, rearview mirrors or side mirrors tends to be low.

For example, the attribute decision part 217 may determine that the attribute of the driver is the first attribute when a count number or an amount of time (may be a count number or an amount of time for a predetermined time) in which the driver sees a speed indicator (a speedometer) disposed in the automobile 1 exceeds a predetermined threshold value. In general, when the driver is the beginner, a frequency that the driver sees the speed indicator tends to be high.

For example, the attribute decision part 217 may determine that the attribute of the driver is the first attribute when an inter-vehicle distance between the host vehicle (the automobile 1) and another vehicle (for example, another vehicle that precedes the host vehicle) is larger than a predetermined threshold value. In general, when the driver is the beginner, the inter-vehicle distance tends to be large.

For example, the attribute decision part 217 may determine that the attribute of the driver is the first attribute when the steering wheel shake is larger than a predetermined threshold value. In general, when the driver is the beginner, the steering wheel shake tends to be large.

For example, the attribute decision part 217 may determine that the attribute of the driver is the first attribute in the case in which the host vehicle (the automobile 1) is not started only when a distance between the host vehicle (the automobile 1) and a facing vehicle (an oncoming vehicle) is larger than a predetermined threshold value. In general, when the driver is the beginner, the host vehicle (the automobile 1) tends to start only when the distance between the host vehicle (the automobile 1) and the oncoming vehicle is large.

For example, the attribute decision part 217 may determine that the attribute of the driver is the first attribute when the automobile 1 is decelerated before a predetermined curve (for example, a curve having a curvature smaller than a predetermined threshold value). In general, when the driver is the beginner, even in the curve having the small curvature, it is likely to decelerate the automobile 1 before the above mentioned curves.

For example, the attribute decision part 217 may determine that the attribute of the driver is the first attribute when a duration in which the automobile 1 does not travel a narrow alley (for example, a road having a width smaller than a predetermined threshold value) continues to be a predetermined duration or more. In general, when the driver is the beginner, the automobile 1 tends not to travel the narrow alley.

For example, the attribute decision part 217 may determine that the attribute of the driver is the first attribute when the automobile 1 travels a central lane in a road having three lanes. In general, when the driver is the beginner, the automobile 1 tends to travel the central lane.

Here, for example, the attribute decision part 217 may determine that the attribute of the driver is the first attribute when at least one of the plurality of conditions for deciding that the attribute of the driver is the first attribute are satisfied, or may determine that the attribute of the driver is the first attribute when a predetermined number or more of the plurality of conditions for deciding that the attribute of the driver is the first attribute are satisfied. A value of two or more is used as the predetermined number.

For example, the attribute decision part 217 may determine that the attribute of the driver is the second attribute, when a count number or an amount of time (may be the count number or the amount of time for a predetermined time) in which a position (a gazing position) of a sight line of the driver is directed far from the automobile 1 by a predetermined threshold value or more exceeds a predetermined threshold value or a count number or an amount of time (may be the count number or the amount of time for a predetermined time) in which a range (a gazing range) including the position to which the sight line of the driver is directed is present far from the automobile 1 by a predetermined threshold value or more exceeds a predetermined threshold value. In general, when the driver is the elderly people, the driver tends to see a far side.

For example, the attribute decision part 217 may determine that the attribute of the driver is the second attribute when a range of a position (a gazing position) to which a sight line of the driver is directed for a predetermined time is a predetermined range or more. In general, when the driver is the elderly people, the driver tends to see a wider range.

For example, the attribute decision part 217 may determine that the attribute of the driver is the second attribute when a time in which a sight line of the driver is deviated from a predetermined object is a predetermined threshold value or more. In general, when the driver is the elderly people, a time in which a sight line of the driver is deviated from an object tends to be longer, i.e., a total search time for the object tends to be longer. Here, for example, one or more of a pedestrian, a vehicle except the host vehicle (the automobile 1), a traffic signal, a pedestrian crossing, another obstacle, and so on, may be provided as the predetermined object.

For example, the attribute decision part 217 may determine that the attribute of the driver is the second attribute when a time in which a sight line of the driver is continuously present at a position (or a predetermined range including the position) of a predetermined object is less than a predetermined threshold value. In general, when the driver is the elderly people, the time in which the driver continuously gazes the object tends to be shorter. Here, for example, one or more of a pedestrian, a vehicle except the host vehicle (the automobile 1), a traffic signal, a pedestrian crossing, another obstacle, and so on, may be provided as the predetermined object.

For example, the attribute decision part 217 may determine that the attribute of the driver is the second attribute when a count number or an amount of time (may be a count number or an amount of time for a predetermined time) in which the driver sees a predetermined place exceeds a predetermined threshold value. In general, when the driver is the elderly people, the driver tends to see the same place many times.

For example, the attribute decision part 217 may determine that the attribute of the driver is the second attribute when a saccadic time (a time of rapid eyeball movement) is shorter than a predetermined threshold value on the basis of sight line information (information related to eyeball movement) of the driver. In general, when the driver is the elderly people, the saccadic time tends to be shorter.

For example, the attribute decision part 217 may determine that the attribute of the driver is the second attribute when a count number or an amount of time (may be a count number or an amount of time for a predetermined time) in which the automobile 1 is traveling a place close to a central lane is larger than a predetermined threshold value. In general, when the driver is the elderly people, the automobile 1 tends to have a higher possibility to drive at a position closer to the central lane.

Here, for example, the attribute decision part 217 may determine that the attribute of the driver is the second attribute when at least one of the plurality of conditions for deciding that the attribute of the driver is the second attribute are satisfied, or may determine that the attribute of the driver is the second attribute when a predetermined number or more of the plurality of conditions for deciding the attribute of the driver is the second attribute are satisfied. A value of two or more is used as the predetermined number.

For example, the attribute decision part 217 may determine that the attribute of the driver is the third attribute, when a count number or an amount of time (may be a count number or an amount of time for a predetermined time) in which a position (a gazing position) of a sight line of the driver is directed far from the automobile 1 by a predetermined threshold value or more exceeds a predetermined threshold value or a count number or an amount of time (may be a count number or an amount of time for a predetermined time) in which a range (a gazing range) including the position to which a sight line of the driver is directed is present far from the automobile 1 by a predetermined threshold value or more exceeds a predetermined threshold value. In general, when the driver is the general driver, the driver tends to see a far side.

Here, for example, the condition is same for the second attribute and the third attribute.

For example, the attribute decision part 217 may determine that the attribute of the driver is the third attribute when a range of a position (a gazing position) to which a sight line of the driver is directed for a predetermined time exceeds a predetermined range or more. In general, when the driver is the general driver, the driver tends to see a wider range.

Here, for example, the condition is same for the second attribute and the third attribute.

For example, the attribute decision part 217 may determine that the attribute of the driver is the second attribute when a count number or amount of time (may be a count number or amount of time for a predetermined time) in which the driver sees a white line on a road is smaller than a predetermined threshold value. In general, when the driver is the general driver, the driver tends not to see the white line so much.

For example, the attribute decision part 217 may determine that the attribute of the driver is the third attribute when a count number or amount of time (may be a count number or amount of time for a predetermined time) in which the driver sees a predetermined mirror exceeds a predetermined threshold value. In general, when the driver is the general driver, the driver tends to frequently see a windshield rearview mirror, rearview mirrors or side mirrors.

For example, the attribute decision part 217 may determine that the attribute of the driver is the third attribute when a range based on a collection of positions (gazing positions) to which a sight line of the driver is directed for a predetermined time becomes a range larger than a predetermined threshold value and distribution of the positions to which the sight line is directed has predetermined uniformity level or more. In general, when the driver is the general driver, a gazing range is wider, and gazing positions are uniformly distributed.

Here, for uniformity of distribution of the positions to which the sight line of the driver is directed, for example, an inverse number of dispersion of the distribution of the positions to which the sight line of the driver is directed may be used.

Here, for example, the attribute decision part 217 may determine that the attribute of the driver is the third attribute when at least one of the plurality of conditions for deciding that the attribute of the driver is the third attribute are satisfied, or determine that the attribute of the driver is the third attribute when a predetermined number or more of the plurality of conditions for deciding that the attribute of the driver is the third attribute are satisfied. A value of two or more is used as the predetermined number.

As an example, the attribute decision part 217 may independently determine that the attribute of the driver is the first attribute, the attribute of the driver is the second attribute, or the attribute of the driver is the third attribute, respectively.

For example, the attribute decision part 217 classifies the predetermined information (may be a piece of information or may be a combination of a plurality of pieces of information), which is used for decision, into three groups (a first group, a second group and a third group), determines that the driver belongs to the first attribute when the information is classified as the first group, determines that the driver belongs to the second attribute when the information is classified as the second group, and determines that the driver belongs to the third attribute when the information is classified as the third group. As a specific example, when the information of the inter-vehicle distance is used for decision, a configuration in which an inter-vehicle distance included in an average range is classified as the third group, an inter-vehicle distance larger than the average range is classified as the first group, and an inter-vehicle distance smaller than the average range is classified as the second group may be used.

As another example, when n (n is a value of two or more) attributes are determine, the attribute decision part 217 may determine whether a driver who is a decision target belongs to any one of (n−1) attributes, and when the driver does not belong to the (n−1) attributes, may determine that the driver belongs to the remaining one attributes. As a specific example, when the three attributes (the first attribute, the second attribute and the third attribute) are determine, the attribute decision part 217 may determine whether the driver who is a decision target belongs to either of the two attributes (for example, the first attribute and the second attribute), and when the driver does not belong to any one of the two attributes, determine that the driver belongs to the third attribute.

Here, arbitrary attributes may be used as the (n−1) attributes in the n attributes.

Here, while the attributes referred to as the beginner, the elderly people and the general driver have been exemplified as described above, other arbitrary attributes may be used as a type of attributes.

For example, attributes referred to as "a driver who performs an action matched to a predetermined action pattern" may be used. The predetermined action pattern may be an arbitrary action pattern, and as an example, an action pattern referred to as that a driver's foot is not placed on a brake (for example, feet are crossed) when the automobile 1 is in an automatic cruise mode can be considered.

Further, information referred to as that the automobile 1 is in the automatic cruise mode may be acquired by, for example, the driving traveling information acquisition part 311. In addition, information referred to as that a driver's foot is not placed on a brake may be acquired by, for example, the driver action information acquisition part 314.

In addition, when the attribute of the driver is determine, the attribute decision part 217 may use or may not use resultant information obtained through learning by the learning part 216.

For example, the attribute decision part 217 may determine the attributes of the driver on the basis of the resultant information through learning by the learning part 216.

In addition, for example, the learning of outputting the decision result of the attributes of the driver as the learning result may be performed by the learning part 216, and the attribute decision part 217 may employ the learning result as the decision result of the attributes.

In this case, for example, the attribute decision part 217 determines the attributes of the driver on the basis of the past information and the current information in the information related to the operation or the like by the driver using the function of the learning part 216. That is, in the embodiment, information (for example, learning resultant information) learned when the driver drove the automobile 1 in the past is stored with respect to the same driver, and current information is acquired while using the stored past information when the driver drives the automobile 1 at the next opportunity, and the learning can be continuously performed by matching the pieces of information (the past information and the current information).

In the function of the learning part 216, for example, with respect to the same driver, a value of the parameter is optimized by continuously updating (learning) a value of a predetermined parameter. Accordingly, with respect to the same driver, according to an increase (or a decrease) in a technique of the driving operation of the driver, a determine attributes can be varied.

In learning using AI, for example, according to a technique of mechanical learning, a feature value related to the attributes of the driver can be uniquely extracted by repeatedly analyzing a large amount of information, figuring out a pattern from the information or performing deep learning, and the attributes of the driver can be determine by performing identification or classification of the driver. Arbitrary information may be used as the information, and in the embodiment, one piece or more of the information acquired by the information acquisition part 214 may be used.

The control condition determination part 218 determines a condition (a control condition) that controls the headlight section 121 (the left headlight 11 and the right headlight 12) on the basis of the attributes determine by the attribute decision part 217.

For example, the control condition determination part 218 may determine to use the control condition by selecting the control condition (for example, one control condition) appropriate for the attributes among the plurality of different control conditions that were previously prepared, or determine to use the control condition by newly generating a control condition appropriate for the attributes.

Here, for example, the control condition may be a condition related to one or more of a low beam, a high beam, a light distribution of ADB, a light quantity, marking light, road surface drawing (drawing light on a road surface), a high illumination band variation, and so on.

The light distribution controller 219 controls a light distribution of the headlight section 121 (the left headlight 11 and the right headlight 12) by controlling radiation of light by the headlight section 121 (the left headlight 11 and the right headlight 12) on the basis of the control condition determined by the control condition determination part 218.

Here, for example, the light distribution controller 219 controls a light distribution when headlight section 121 (the left headlight 11 and the right headlight 12) is turned on, or a light distribution when the headlight section 121 (the left headlight 11 and the right headlight 12) is flickered.

Configuration in the Vicinity of Driver's Seat for Automobile

Figure 3:
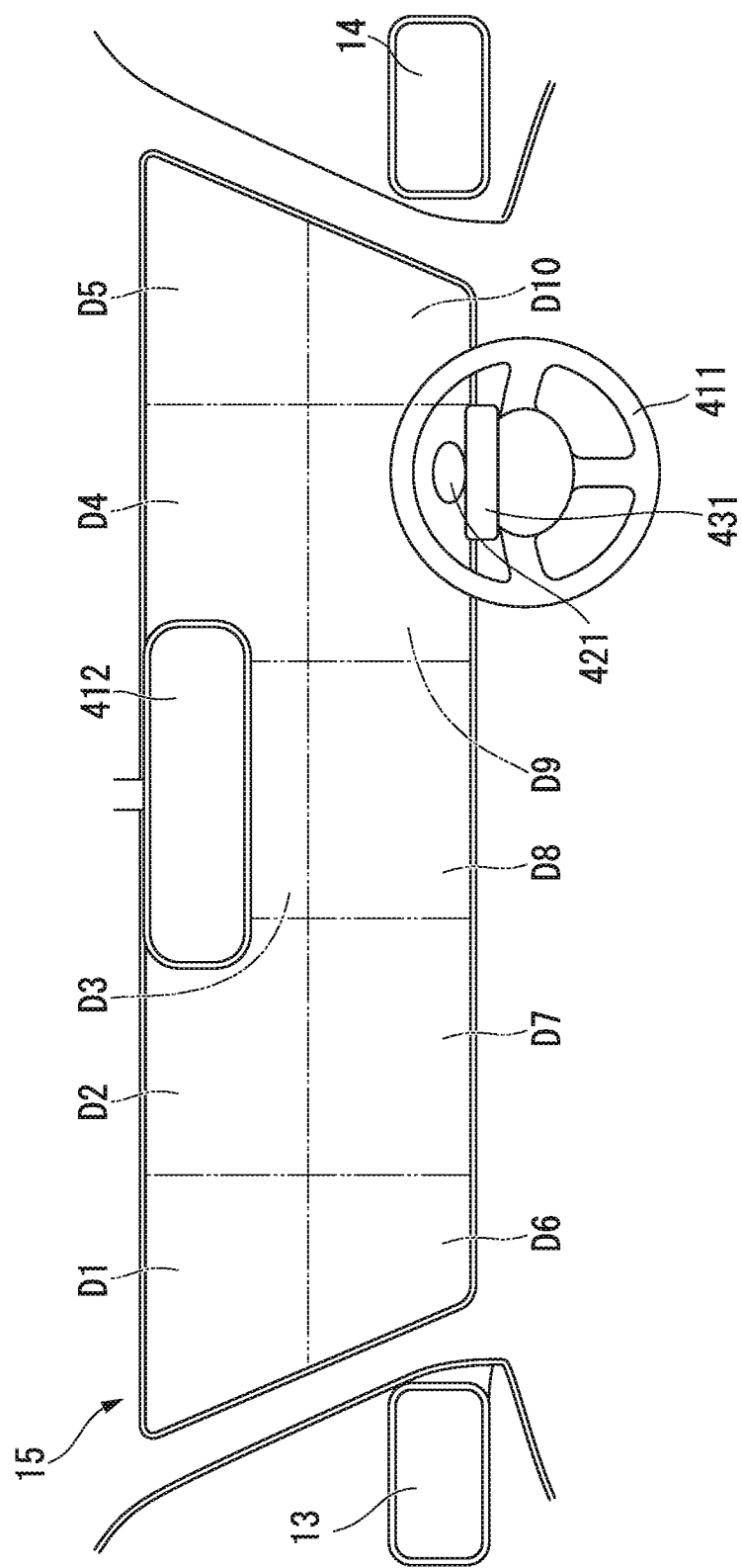
FIG. 3 is a view showing a schematic configuration of the vicinity of a driver's seat of the automobile according to the embodiment of the present invention.

FIG. 3 is a view showing a schematic configuration in the vicinity of the driver's seat for the automobile 1 according to the embodiment of the present invention.

FIG. 3 shows the left side mirror 13, the right side mirror 14, the front window 15, a handle 411, a windshield rearview mirror 412, a camera 421 and a sight line sensor 431.

In addition, FIG. 3 shows divided regions D1 to D10 as region (grids) in which the region of the front window 15 is virtually divided into 10 regions. In the embodiment, the front window 15 is not really divided and is divided into the divided regions D1 to D10 as control units.

For example, the camera 421 is an example of a functional unit included in the vehicle front outside detector 21 shown in FIG. 1. In the example of FIG. 3, the camera 421 is provided in the vicinity of the driver's seat in the automobile 1, and for example, installed in front of the speed indicator in the vicinity of a fixed portion of the handle 411.

The camera 421 images information of an image of a scene (a foreground) seen at a side in front of the outside of the automobile 1.

For example, the sight line sensor 431 is an example of a functional unit included in the vehicle inside detector 23 shown in FIG. 1. In an example of FIG. 3, the sight line sensor 431 is provided in the vicinity of the driver's seat in the automobile 1, and for example, provided in front of the speed indicator in the vicinity of the fixed portion of the handle 411.

The sight line sensor 431 detects information related to a sight line of the driver who sits on the driver's seat in the automobile 1.

Here, for example, the sight line sensor 431 may be constituted by a light emitting diode (LED) that outputs infrared light and a camera that can detect the infrared light. The sight line sensor 431 illuminates the driver's face using infrared light from the LED, captures the infrared light using the camera, and measures (detects) a sight line of the driver.

As an example, in the controller 31 (the attribute decision part 217 or the like), since an image (a foreground image) captured by the camera 421 overlaps (overlays) a sight line detected by the sight line sensor 431, a place to which the driver sees can be specified.

As another example, in the controller 31 (the attribute decision part 217 or the like), a place to which the driver sees (in the example, a divided region) can be specified by specifying one divided region to which a sight line detected by the sight line sensor 431 is directed, among the plurality of divided regions D1 to D10 virtually formed in the front window 15. Here, for example, correspondence between various directions of the sight line and the divided regions corresponding to the directions of the sight line may be previously set to the controller 31 (for example, the storage 213). Accordingly, simply, an approximate directivity of the sight line of the driver can be recognized.

Further, an arbitrary number may be used as the number to which the front window 15 is divided into a plurality of regions.

Correspondence Between Attributes and Control Condition

Figure 4:
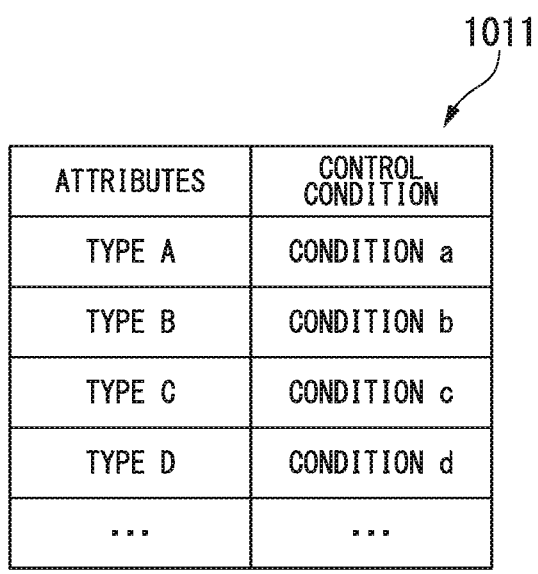
FIG. 4 is a view showing an example of a correspondence table between attributes and control conditions according to the embodiment of the present invention.

FIG. 4 is a view showing an example of a correspondence table 1011 between attributes and control conditions according to the embodiment of the present invention.

In the embodiment, for example, the correspondence table 1011 is previously stored in the storage 213 of the controller 31.

In the correspondence table 1011, one or more attributes and one control condition are correspondingly stored.

In the example of FIG. 4, in the correspondence table 1011, attributes of "a type A" (for example, a first attribute) correspond to a condition a (for example, a first control condition). In addition, attributes of "a type B" (for example, a second attribute) correspond to a condition b (for example, a second control condition), attributes of "a type C" (for example, a third attribute) correspond to a condition c (for example, a third control condition), and the same applies to the following description.

Here, the contents of the condition used for determining the attributes are also, for example, previously stored in the storage 213 of the controller 31.

In addition, the contents of the control conditions are also, for example, previously stored in the storage 213 of the controller 31.

In the embodiment, the control condition determination part 218 may determine to use the control condition corresponding to the attributes determine by the attribute decision part 217 on the basis of the contents in the correspondence table 1011.

Here, arbitrary correspondence may be used as the correspondence between the attributes and the control conditions.

As a specific example, the control condition such as radiation of light from the headlight section 121 (the left headlight 11 and the right headlight 12) to a farther side (compared to the general driver) may correspond to the attributes referred to as "the beginner." Accordingly, for example, it is possible to guide an orientation of the sight line of the driver as "the beginner" to a far side, it is possible to provide a vision to a beginner such as an expert looking the far side, and it can be useful for improving safety at night.

As another specific example, a control condition such as performing a marking to an object which should be seen by using light from the headlight section 121 (the left headlight 11 and the right headlight 12) may correspond to the attributes referred to as "the elderly people". Accordingly, for example, it is possible to securely urge the driver who is the elderly people to visually recognize the object which should be seen. Further, marking the object to be seen is realized by illuminating the object with the light to emphasize the object.

As another specific example, with respect to the attribute referred to as "the general driver", a control condition may be corresponded in which light from the headlight section 121 (the left headlight 11 and the right headlight 12) is distributed in an average distribution for most of the people.

In addition, as another specific example, a control condition in which light from the headlight section 121 (the left headlight 11 and the right headlight 12) is distributed to attract attention to a driver may correspond to the attributes referred to as "a driver's foot is not placed on a brake." As an example of such a light distribution, when a T-shaped light distribution is used, a light distribution in which a marginal portion (a line segment in a longitudinal direction along a direction of advance of the automobile 1) is longer (than a predetermined reference) may be used. That is, in this case, since it is expected that a time required until the driver steps on a brake is longer (in comparison with the case in which a driver's foot is placed on the brake), this point is noticed to the driver.

Example of Procedure of Processing Performed in Controller

Figure 5:
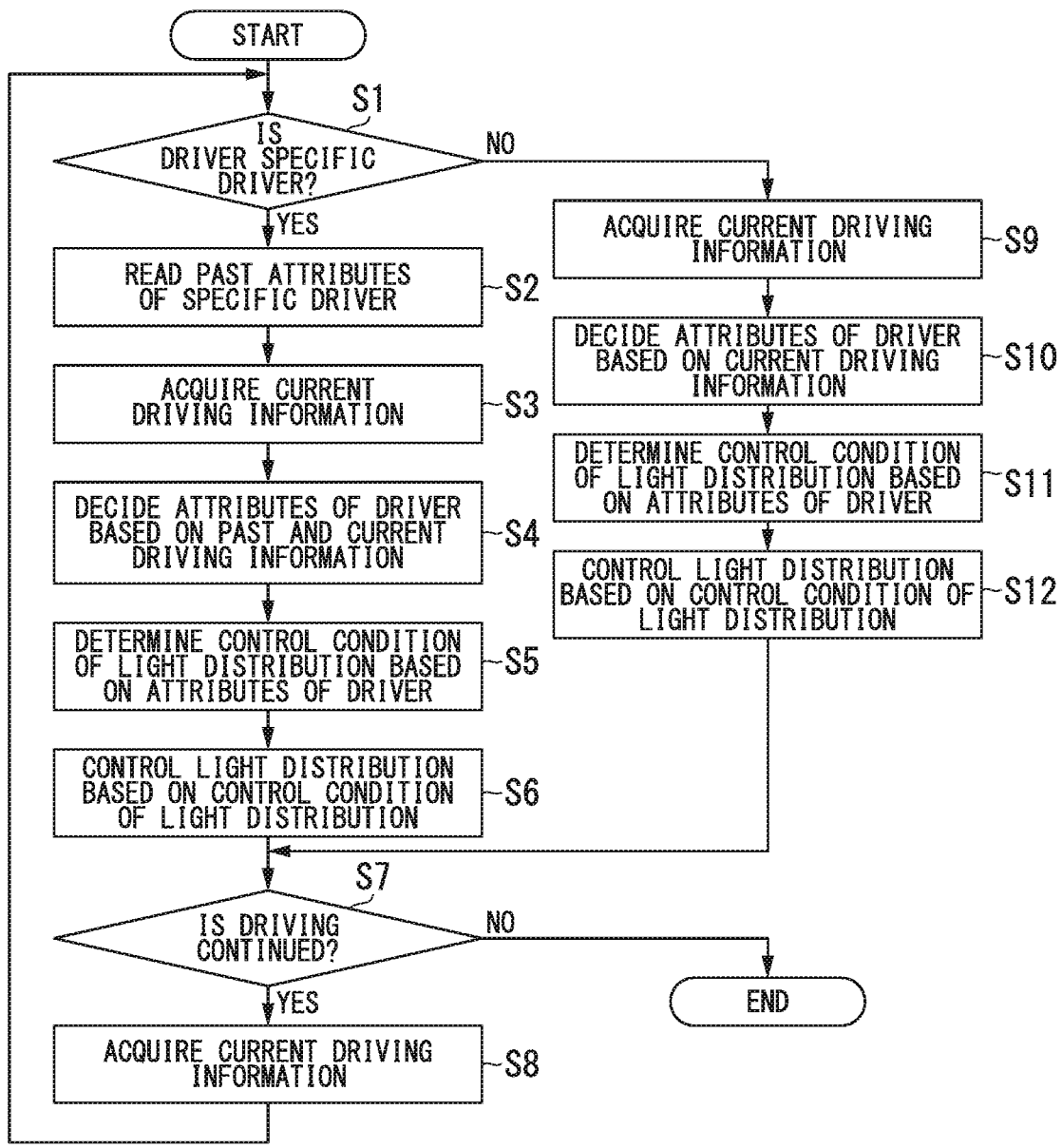
FIG. 5 is a flowchart showing an example of a procedure of processing performed in a controller according to the embodiment of the present invention.

FIG. 5 is a flowchart showing an example of a procedure of processing performed in the controller 31 according to the embodiment of the present invention.

In the example, it is assumed that a certain person gets on the driver's seat in the automobile 1 as a driver.

In addition, in the example, a specified driver is referred as a driver who is already recognized in the controller 31. The specified driver is, for example, a person who has driven the automobile 1 in the past, or a person who has not driven the automobile 1 in the past but has information related to the person stored in the controller 31 (for example, the storage 213).

(Step S1)

The driver identification part 215 identifies whether a person who gets on the driver's seat (the driver at this time) is the specified driver.

As a result, the driver identification part 215 advances to processing of step S2 when the person is identified as the specified driver (step S1: YES).

On the other hand, as a result, the driver identification part 215 advances to processing of step S9 when the person is not identified as the specified driver (step S1: NO).

(Step S2)

The attribute decision part 217 reads the past attributes (for example, the last assigned attributes) with respect to the identified specified driver. Then, the procedure advances to processing of step S3.

Here, when the learning by the learning part 216 is performed, the attribute decision part 217 may notify the read attributes to the learning part 216. The learning part 216 may use the notified attributes in the learning.

Further, when the past attributes are not used with respect to the identified specified driver, the processing of step S2 may be omitted.

(Step S3)

The attribute decision part 217 acquires the current driving information as the information related to driving by the driver (in the example, referred to as "driving information"). Then, the procedure advances to processing of step S4.

Here, for example, one or more pieces of arbitrary information acquired by the information acquisition part 214 may be used as the driving information.

(Step S4)

The attribute decision part 217 determines the attributes of the driver on the basis of the past driving information and the current driving information. Then, the procedure advances to processing of step S5.

Here, for example, the attribute decision part 217 acquires the past driving information with respect to the identified driver (the specified driver) from the storage 213.

(Step S5)

The control condition determination part 218 determines the control condition of the light distribution on the basis of the attributes of the driver determined by the attribute decision part 217. Then, the procedure advances to processing of step S6.

(Step S6)

The light distribution controller 219 controls the light distribution of the headlight section 121 (the left headlight 11 and the right headlight 12) on the basis of the control condition of the light distribution determined by the control condition determination part 218. Then, the procedure advances to processing of step S7.

(Step S7)

In the controller 31 (for example, the driver identification part 215 or the like), it is determine whether the driving of the automobile 1 by the current driver is continued.

As a result, in the controller 31 (for example, the driver identification part 215 or the like), when it is determined that the driving of the automobile 1 by the current driver is continued (step S7: YES), the procedure advances to processing of step S8.

On the other hand, in the controller 31 (for example, the driver identification part 215 or the like), when it is determined that the driving of the automobile 1 of the current driver is not continued (step S7: NO), processing of the flow is terminated.

Here, in the example, in the controller 31, it is determined that the driving is not continued (i.e., the driving is terminated) when the predetermined condition is satisfied, and it is determined that the driving is continued in the other case. An arbitrary condition may be used as the predetermined condition, and for example, a condition in which the engine in the automobile 1 was turned off, a condition in which a driver got off from the driver's seat in the automobile 1, or the like, may be used.

(Step S8)

The attribute decision part 217 acquires the current driving information. Then, the procedure returns to the processing of step S1.

Further, while the configuration in which the procedure returns to the processing of step S1 after the processing of step S8 has been described in the example, as another configuration example, when the procedure has passed through the processing of step S2 to step S6, a configuration in which the procedure returns to another processing (for example, the processing of step S4) after the processing of step S8 may be used.

(Step S9)

The attribute decision part 217 acquires the current driving information as the information (driving information) related to the driving by the driver (here, not the specified driver, for example, an unknown driver). Then, the procedure advances to processing of step S10.

(Step S10)

The attribute decision part 217 determines attributes of a driver on the basis of the current driving information. Then, the procedure advances to processing of step S11.

(Step S11)

The control condition determination part 218 determines a control condition of a light distribution on the basis of the attributes of the driver determine by the attribute decision part 217. Then, the procedure advances to processing of step S12.

(Step S12)

The light distribution controller 219 controls a light distribution of the headlight section 121 (the left headlight 11 and the right headlight 12) on the basis of the control condition of the light distribution determined by the control condition determination part 218. Then, the procedure returns to the processing of step S7.

Further, in the example, when the procedure has passed through the processing of step S9 to step S12, in the processing of step S1 of the next time, it is determined that the driver is the specified driver. That is, when a person who is not the specified driver drives the automobile 1, while the procedure passes through the processing of step S9 to step S12 at the first time, the procedure passes through step S2 to step S6 from the next time.

In the example, in the controller 31 (for example, the driver identification part 215 or the like), when a person who is not the specified driver drives the automobile 1, in the processing of step S9 to step S12, for example, the person is stored (registered) on the storage 213 as the specified driver. In this case, for example, the person is specified by one or more among pieces of bio-information or the like such as some or all of driving information, driver ID input from the person, information of the person's face, or the like.

Summary of Embodiment

As described above, in the headlight control system 101 of the automobile 1 according to the embodiment, in the controller 31, the attributes of the driver can be accurately determine by deciding the attributes of the driver on the basis of a motion of at least a part of the driver (for example, a motion of a sight line of a driver, a motion of a driver's face, another action of a driver, or the like).

In addition, in the controller 31, when the attribute of the driver is determined, the attributes of the driver can be more accurately determined by further considering information related to the outside of the automobile 1 (vehicle outside), past information related to the driver, or the like.

In addition, in the controller 31, a light distribution that supports the driver according to personality (the attributes) of the driver can be realized by controlling radiation of light from the headlight section 121 (the left headlight 11 and the right headlight 12) so that the light distribution becomes a light distribution which is appropriate with respect to the attributes of the driver.

Here, in the controller 31, when the attribute of the driver is determined, in consideration of a traffic circumstance (a traffic scene), the attributes of the driver can be accurately determined according to the traffic circumstance, and a light distribution can be controlled according to the traffic circumstance.

In addition, in the controller 31, with respect to the same driver, for example, in comparison with the case in which the attributes of the driver and the light distribution are fixed, decision of the attributes and control of the light distribution which are more suitable for the actual circumstances can be performed by updating the attributes assigned to the driver and by updating a light distribution controlled with respect to the driver.

Configuration Example

As a configuration example, there is provided a control device for a vehicle headlight (in the embodiment, the controller 31) including a motion information acquisition part (in the embodiment, for example, the sight line information acquisition part 313, the driver action information acquisition part 314 and the face direction angular speed information acquisition part 315) that acquires information of a motion of at least a part of a driver in the vehicle (in the embodiment, the automobile 1), the attribute decision part (in the embodiment, the attribute decision part 217) that determines the attribute of the driver based on the information acquired by the motion information acquisition part, and a light distribution controller (in the embodiment, the light distribution controller 219) that controls a light distribution of the vehicle headlight (in the embodiment, the left headlight 11 and the right headlight 12) based on the attribute determine by the attribute decision part.

As a configuration example, the control device for a vehicle headlight includes a vehicle outside information acquisition part (in the embodiment, for example, the photographing information acquisition part 312 and the object information acquisition part 316) that acquires information regarding the outside of the vehicle, wherein, when determining the attribute, the attribute decision part determines the attribute of the driver based on the information acquired by the vehicle outside information acquisition part.

As a configuration example, the control device for a vehicle headlight includes a driver identification part (in the embodiment, the driver identification part 215) that identifies the driver, wherein, when determining the attribute, the attribute decision part determines the attribute of the driver based on past information regarding the driver identified by the driver identification part.

The processing may be performed by recording a program for realizing a function of an apparatus according to the above-mentioned embodiment (for example, the controller 31 or the like) on a computer-readable recording medium, and reading and executing the program recorded on the recording medium using a computer system.

Further, "the computer system" disclosed herein may include hardware such as an operating system (OS), peripheral devices, or the like.

In addition, "the computer-readable recording medium" is referred to as a storage device, for example, an erasable and writable non-volatile memory such as a flexible disk, a magneto-optic disk, a read only memory (ROM), a flash memory, or the like, a portable medium such as a digital versatile disc (DVD) or the like, a hard disk or the like installed in the computer system, and so on.

Further, "the computer-readable recording medium" includes a medium that holds a program for a certain time, for example, a volatile memory (for example, a dynamic random access memory (DRAM)) in a computer system that is a server or a client when a program is transmitted via a network such as the Internet or the like, or a communication line of a telephone line.

In addition, the program may be transmitted to another computer system from the computer system in which the program is stored in the storage device or the like via a transmission medium or using transmitted waves in the transmission medium. Here, "the transmission medium" through which the program is transmitted is referred to as a medium having a function of transmitting the information, for example, a network (a communication network) such as the Internet or the like, or a communication line (a communication wire) such as a telephone line or the like.

In addition, the program may be a program for realizing a part of the above-mentioned function. Further, the program may be a so-called differential file (differential program) that can be realized by a combination between the above-mentioned function and the program that is already recorded on the computer system.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A control device for a vehicle headlight, the control device comprising:
   a motion information acquisition part that acquires information of a motion of at least a part of a driver in the vehicle;
   a vehicle outside information acquisition part that acquires information regarding an outside of the vehicle;
   a vehicle information detector that detects information regarding the vehicle based on one or more of a sensor configured to detect information related to an operation amount of an accelerator of the vehicle, a sensor configured to detect information related to an operation amount of a brake of the vehicle, a sensor configured to detect information related to an operation amount of a steering wheel of the vehicle, a sensor configured to detect information related to a speed of the vehicle, a sensor configured to detect information related to an acceleration of the vehicle, and a sensor configured to detect information related to a steering torque of the vehicle,
   an attribute decision part that determines attribute of the driver based on at least the information acquired by the motion information acquisition part, the information acquired by the vehicle outside information acquisition part and the vehicle information detector; and
   a light distribution controller that controls a light distribution of the vehicle headlight based on the attribute determined by the attribute decision part.

2. A vehicle headlight, comprising:
   a headlight that is capable of variably changing a light distribution, and
   the control device for a vehicle headlight according to claim 1 that controls the headlight.

3. The control device for a vehicle headlight according to claim 1, further comprising: a driver identification part that identifies the driver,
   wherein, when determining the attribute, the attribute decision part determines the attribute of the driver also based on past information regarding the driver identified by the driver identification part.

4. The control device for a vehicle headlight according to claim 1,
   wherein the vehicle outside information acquisition part includes at least one of a photographing information acquisition part that acquires information of a captured image and an object information acquisition part that acquires information related to an object present outside of the vehicle.

5. The control device for a vehicle headlight according to claim 1,
wherein the motion information acquisition part includes at least one of a sight line information acquisition part that acquires information related to a sight line of the driver, a driver action information acquisition part that acquires information related to an action of the driver, and a face direction angular speed information acquisition part that acquires information related to a direction of the driver's face.

6. The control device for a vehicle headlight according to claim 4,
wherein the information acquired by the vehicle outside information acquisition part includes information of a distance between the vehicle operated by the driver and another vehicle.

7. The control device for a vehicle headlight according to claim 3,
wherein the motion information acquisition part includes at least one of a sight line information acquisition part that acquires information related to a sight line of the driver, a driver action information acquisition part that acquires information related to an action of the driver, and a face direction angular speed information acquisition part that acquires information related to a direction of the driver's face.

8. The control device for a vehicle headlight according to claim 4,
wherein the information acquired by the vehicle outside information acquisition part includes information regarding which lane the vehicle operated by the driver is traveling on a road.

9. A control device for a vehicle headlight, the control device comprising:
a vehicle outside information acquisition part that acquires information regarding an outside of the vehicle;
a driver identification part that identifies the driver;
an attribute decision part that determines attribute of the driver based on the information acquired by the vehicle outside information acquisition part; and
a light distribution controller that controls a light distribution of the vehicle headlight based on the attribute determined by the attribute decision part,
wherein, when determining the attribute, the attribute decision part determines the attribute of the driver based on at least the information acquired by the vehicle outside information acquisition part and past information regarding the driver identified by the driver identification part.

10. The control device for a vehicle headlight according to claim 9, further comprising: a motion information acquisition part that acquires information of a motion of at least a part of a driver in the vehicle,
wherein, when determining the attribute, the attribute decision part determines the attribute of the driver based on at least the information acquired by the motion information acquisition part and the information acquired by the vehicle outside information acquisition part.

11. The control device for a vehicle headlight according to claim 10, further comprising: a driver identification part that identifies the driver,
wherein, when determining the attribute, the attribute decision part determines the attribute of the driver based on at least the information acquired by the motion information acquisition part, the information acquired by the vehicle outside information acquisition part and past information regarding the driver identified by the driver identification part.

12. The control device for a vehicle headlight according to claim 10,
wherein the motion information acquisition part includes at least one of a sight line information acquisition part that acquires information related to a sight line of the driver, a driver action information acquisition part that acquires information related to an action of the driver, and a face direction angular speed information acquisition part that acquires information related to a direction of the driver's face.

13. The control device for a vehicle headlight according to claim 9,
wherein the vehicle outside information acquisition part includes at least one of a photographing information acquisition part that acquires information of a captured image and an object information acquisition part that acquires information related to an object present outside of the vehicle.

14. The control device for a vehicle headlight according to claim 13,
wherein the information acquired by the vehicle outside information acquisition part includes information of a distance between the vehicle operated by the driver and another vehicle.

15. The control device for a vehicle headlight according to claim 13,
wherein the information acquired by the vehicle outside information acquisition part includes information regarding which lane the vehicle operated by the driver is traveling on a road.

16. A vehicle headlight, comprising:
a headlight that is capable of variably changing a light distribution, and
the control device for a vehicle headlight according to claim 9 that controls the headlight.

* * * * *